United States Patent
Steiger

(10) Patent No.: US 10,602,763 B2
(45) Date of Patent: Mar. 31, 2020

(54) PROCESS FOR IRON SUPPLEMENTATION OF BEVERAGES

(75) Inventor: Georg Steiger, Kaiseraugst (CH)

(73) Assignee: DSM IP ASSETS BV, Heerlen (NL)

(*) Notice: Subject to any disclaimer, the term of this patent is extended or adjusted under 35 U.S.C. 154(b) by 450 days.

(21) Appl. No.: 13/985,775

(22) PCT Filed: Mar. 9, 2012

(86) PCT No.: PCT/EP2012/054086
§ 371 (c)(1),
(2), (4) Date: Aug. 15, 2013

(87) PCT Pub. No.: WO2012/120110
PCT Pub. Date: Sep. 13, 2012

(65) Prior Publication Data
US 2013/0330459 A1 Dec. 12, 2013

(30) Foreign Application Priority Data
Mar. 10, 2011 (EP) .................................... 11157624

(51) Int. Cl.
| | | |
|---|---|---|
| *A23L 1/00* | (2006.01) | |
| *A23L 33/16* | (2016.01) | |
| *A23L 2/52* | (2006.01) | |
| *A23C 9/152* | (2006.01) | |
| *A23L 2/02* | (2006.01) | |
| *A61K 31/19* | (2006.01) | |

(52) U.S. Cl.
CPC ............ *A23L 33/16* (2016.08); *A23C 9/1522* (2013.01); *A23L 2/02* (2013.01); *A23L 2/52* (2013.01); *A61K 31/19* (2013.01); *A23V 2002/00* (2013.01)

(58) Field of Classification Search
CPC .......... A23V 2002/00; A23V 2250/032; A23V 2250/1592; A23V 2250/211; A23V 2250/628; A23C 9/1522; A23L 2/02; A23L 2/52; A23L 33/16; A61K 31/19
See application file for complete search history.

(56) References Cited

U.S. PATENT DOCUMENTS

| | | | |
|---|---|---|---|
| 6,616,955 B2 * | 9/2003 | Nunes ....................... | A23L 2/52 424/439 |
| 2004/0171624 A1 * | 9/2004 | Ozeki .................... | A61K 31/52 514/263.4 |
| 2007/0148259 A1 * | 6/2007 | Gupta ................... | A23L 33/175 424/604 |
| 2009/0023686 A1 * | 1/2009 | McCall, Jr. .......... | A61K 31/194 514/106 |
| 2009/0035385 A1 * | 2/2009 | Bortz .................... | A61K 31/19 424/604 |
| 2009/0124572 A1 | 5/2009 | Nelson | |
| 2011/0021629 A1 | 1/2011 | Nelson et al. | |

FOREIGN PATENT DOCUMENTS

| | | |
|---|---|---|
| CN | 101384295 | 3/2009 |
| JP | 2006-061064 | 3/2006 |
| JP | 2009-292798 | 6/2008 |
| JP | 2008-52442 | 7/2008 |
| JP | 2008-52445 | 7/2008 |
| JP | 2009-136187 | 6/2009 |
| WO | WO2005-084461 | 9/2005 |
| WO | WO2005-107734 | 11/2005 |
| WO | WO 2007/075877 | 7/2007 |

OTHER PUBLICATIONS

International Search Report for PCT/EP2012/054086, dated Apr. 25, 2012.
Chinese Official Action dated May 8, 2014.
Japanese Official Action dated Jun. 16, 2015.
Office Action issued in KR Appln. No. 2013-7022982 dated Aug. 6, 2018 (translation only).

* cited by examiner

*Primary Examiner* — Tamra L. Dicus
(74) *Attorney, Agent, or Firm* — Nixon & Vanderhye P.C.

(57) ABSTRACT

The present invention is directed to a new process for supplementation of beverages with soluble and bio available iron in the form of ferric pyrophosphate. This process allows iron supplementation of beverages at low cost, without affecting either the original taste or the colour of the beverages. It is also directed to a concentrate ferric pyrophosphate-citrate solution and its use in the preparation of an iron enriched beverage. The invention also relates to a beverage obtainable by this process.

8 Claims, No Drawings

PROCESS FOR IRON SUPPLEMENTATION OF BEVERAGES

This application is the U.S. national phase of International Application No. PCT/EP2012/054086, filed 9 Mar. 2012, which designated the U.S. and claims priority to EP Application No. 11157624.5, filed 10 Mar. 2011, the entire contents of each of which are hereby incorporated by reference.

The present invention is directed to a new process for supplementation of beverages with soluble and bio available iron in the form of ferric pyrophosphate. This process allows iron supplementation of beverages at low cost, without affecting either the original taste or the colour of the beverages. It is also directed to a concentrate ferric pyrophosphate-citrate solution and its use in the preparation of an iron enriched beverage. The invention also relates to a beverage obtainable by this process.

Food fortification programmes are usually considered the most cost-effective and sustainable approach to combat iron (Fe) deficiency. However, the success of a Fe fortification programme depends largely on the careful choice of the Fe compound. A cheap and highly bio available Fe compound that causes no organoleptic changes would be the ideal fortification compound. Unfortunately, the water soluble compounds, which are the most bio available, as for example, ferrous sulphate often cause unacceptable colour of flavour changes in the food vehicle as is not usable in beverages (Hurrel & Cook, 1990, Trends Food Sci. Technol. 1:56-61). On the other hand ferric pyrophosphate, at neutral pH, is a known nearly water-insoluble Fe compound often used in the food industry to fortify infant cereals and chocolate drink powders. Its main advantage is that it causes no adverse colour and limited flavour changes to food vehicles. However, it is poorly soluble in organic acids like acetic acid or citric acid but soluble in mineral acid, such as the gastric juice. It remains only partially absorbed in man, especially those with low gastric juice acidity. A further disadvantage of ferric pyrophosphate is that it cannot be used to fortify beverages due to its water insolubility.

Recently, a micronized dispersible ferric pyrophosphate has been developed for food fortification (U.S. Pat. No. 6,616,955). It is based on ferric pyrophosphate particles specially formulated with emulsifiers. This product is dispersible in water, but nevertheless, since the particles are not truly dissolved, the bioavailability of the product remains limited. Moreover, the supplementation cost does not allow the beverage industry to develop beverages supplemented in bio available iron suitable for developing countries or targeting populations with low income.

The inventor of the present application now surprisingly found a new process to solubilise ferric pyrophosphate, which allows generating an aqueous ferric pyrophosphate concentrate at nearly neutral pH (comprised between pH 5-7) where the ferric pyrophosphate is completely soluble and which does not create any off flavour or unpleasant colour change when used to supplement beverages containing up to 15 mg Fe/250 ml. Not only this process allows solubilising ferric pyrophosphate, but upon cooling and storage, ferric pyrophosphate remains in solution. Moreover, the Fe supplemented beverages produced according to the present invention are cheap and compatible with iron supplementation in developing countries when compared to the technologies available today in the industry.

Therefore, the present invention provides a process for the preparation of an aqueous soluble ferric pyrophosphate concentrate, wherein said process comprising the steps of:

(a) adding 0.1 to 5 weight/volume % ferric pyrophosphate to water,
(b) adding 0.15 to 50 weight volume % citrate salt to the dispersion from (a),
(c) heating the resulting solution from (b) until complete dissolution of ferric pyrophosphate As a comparison, ferric pyrophosphate cooked with citric acid does not dissolve completely as obviously insoluble orthophosphates are formed during cooking at low acidic pH. Surprisingly ferric pyrophosphate completely dissolves in a hot aqueous solution of tri sodium citrate at a pH of about 6, and only in the conditions described above.

The pH of the aqueous soluble ferric pyrophosphate concentrate is comprised between 4 to 8, preferably the pH is neutral to slightly basic and comprised between 5 to 8.

The term "aqueous solution" as used herein relates to a solution in which the solvent is water. The word aqueous means pertaining to, related to, similar to, or dissolved in water. Water is an ubiquitous solvent and obviously the most preferred solvent in the beverage industry.

Ferric pyrophosphate also called diphosphoric acid iron (III) salt (CAS: 10058-44-3), monosodium citrate (CAS: 18996-35-5), trisodium citrate (CAS: 68-04-2) can all be purchased from Spectrum Chemical.

In a preferred embodiment, the ferric pyrophosphate is added to water in a concentration comprised between 0.4 and 2 weight/volume %, even more preferably it is comprised between 0.5 and 0.8 weight/volume %. At this concentration, ferric pyrophosphate is completely insoluble in water, and forms a white and turbid dispersion.

In another embodiment, and independently of the ferric pyrophosphate concentration, the preferred amount of citrate salt, is comprised between 4 and 20 weight/volume %. Even more preferably, it is comprised between 4 and 10 weight/volume %.

In another embodiment, the process according to the present invention is characterized in that the weight ratio of ferric pyrophosphate to citrate salt, is comprised between 0.01 and 1, more preferably, between 0.05 and 0.5. This specific ratio is selected for the capacity of citrate salt to contribute to solubilisation of ferric pyrophosphate at neutral or slightly basic pH.

The preferred citrate salt according to the present invention is selected from mono sodium citrate, and tri sodium citrate. Most preferred salt is trisodium citrate in view of its power to solubilise ferric pyrophosphate upon heating.

In another embodiment, the process according to the present invention is characterized in that the heating step of step (c) is performed by heating the solution at a temperature comprised between 80 to 120° C. for 10 to 120 minutes. Preferably the heating step is performed by boiling around 100° C. under atmospheric pressure until ferric pyrophosphate is completely solubilised. Usually this is done within 30 to 60 minutes. The heating step can optionally be performed under pressure. In such a case, the person skilled in the art will of course reduce the heating time accordingly depending on the pressure and temperature applied.

In another embodiment, the present invention also relates to an aqueous soluble ferric pyrophosphate concentrate obtainable by the process of the present invention. Preferable pH of the solution is comprised between 5 and 8. The aqueous soluble ferric pyrophosphate concentrate according to the invention preferably comprises 0.25 to 12.5 g Fe/l.

In yet another embodiment, the present invention relates to the use of an aqueous concentrate according to the present invention for the production of a beverage supplemented with 1 to 60 mg Fe/litre. Preferred beverages according to the present invention are selected from juice, non carbonated soft drink, milk and fruit juice.

The invention is further illustrated by the following examples.

EXAMPLES

Example 1: Preparation of an Orange Juice Supplemented with Soluble Ferric Pyrophosphate For 250 Litre Orange Juice 18 g Ferric Pyrophosphate and 180 g Tri sodium citrate are dissolved in 3 litre of boiling water. This iron concentrate is stirred and heated until completely dissolved. Then the solution is cooled down and added to 250 litre orange juice. The final drink might be pasteurized.

This drink contains 4.5 mg bioavailable and dissolved iron in 250 ml ready drink.

Example 2: Preparation of Milk Supplemented with Soluble Ferric Pyrophosphate For 250 Litre Milk 18 g Ferric pyrophosphate and 180 g Tri sodium citrate are dissolved in 3 litre of boiling water. This iron concentrate is stirred and heated until completely dissolved. Then the solution is cooled down and added to 250 litre milk just before pasteurization. This drink contains 4.5 mg added and about 0.2 mg intrinsic iron in 250 ml ready milk.

Example 3: Preparation of Juice Drink Supplemented with Soluble Ferric Pyrophosphate For 1000 Litre Juice Drink 72 g Ferric pyrophosphate and 720 g Tri sodium citrate are dissolved in 12 litre of boiling water. This iron concentrate is stirred and heated until completely dissolved. Then the solution is cooled down 156 kg of sugar syrup 64° Bx, 200 g ascorbic acid, 6 kg citric acid 50% aqueous solution, quantum satis flavour (e.g. orange) and 3 kg of a 1% aqueous stock solution of Beta carotenen 10% CWS/S and step by step added to 200 l water, and carefully mixed without the use of a high speed mixer. Then the cooled down iron solution is added. This syrup is mixed, diluted to 1000 litre and pasteurized.

The invention claimed is:

1. A process for the preparation of an aqueous soluble ferric pyrophosphate concentrate solution, wherein the process comprises the steps of:
   (a) forming an aqueous dispersion of insoluble ferric pyrophosphate by adding 0.1 to 5 weight/volume % of the insoluble ferric pyrophosphate to water,
   (b) adding 0.15 to 50 weight/volume % of trisodium citrate to the aqueous dispersion obtained from (a) to form an aqueous ferric pyrophosphate and trisodium citrate solution, and
   (c) boiling the resulting aqueous ferric pyrophosphate and trisodium citrate solution from step (b) by heating the aqueous ferric pyrophosphate and trisodium citrate solution at a temperature of 100 to 120° C. and a pH of between 4 to 8 for a time of 10 to 120 minutes until complete dissolution of ferric pyrophosphate occurs to thereby obtain an aqueous soluble ferric pyrophosphate concentrate solution.

2. The process according to claim 1, wherein step (a) is practiced to achieve a concentration of ferric pyrophosphate in the aqueous dispersion of between 0.4 and 2 weight/volume %.

3. The process according to claim 1, wherein step (b) is practiced to achieve a concentration of the trisodium citrate in the solution of between 4 and 20 weight/volume %.

4. The process according to claim 1, wherein the ferric pyrophosphate and the trisodium citrate are present in amounts to achieve a ratio of the ferric pyrophosphate to the trisodium citrate of between 0.01 and 1.

5. The process according to claim 4, wherein the weight ratio of ferric pyrophosphate to trisodium citrate is between 0.05 and 0.5.

6. The process according to claim 1, wherein step (c) is practiced at a pH of about 6.

7. The process according to claim 1, wherein step (a) is practiced by adding the ferric pyrophosphate and the trisodium citrate to boiling water.

8. The process according to claim 7, wherein step (a) is practiced to achieve a concentration of ferric pyrophosphate in the aqueous dispersion of between 0.4 and 2 weight/volume %.

* * * * *